US010006932B2

(12) United States Patent
White et al.

(10) Patent No.: US 10,006,932 B2
(45) Date of Patent: Jun. 26, 2018

(54) ACCELERATION COMPENSATION OF LOAD SENSORS

(71) Applicant: TA Instruments—Waters L.L.C., Milford, MA (US)

(72) Inventors: Andrew D. White, Minneapolis, MN (US); David Deviley, Apple Valley, MN (US); David L. Dingmann, St. Paul, MN (US)

(73) Assignee: TA Instruments-Waters L.L.C., Milford, MA (US)

( * ) Notice: Subject to any disclaimer, the term of this patent is extended or adjusted under 35 U.S.C. 154(b) by 55 days.

(21) Appl. No.: 15/171,742

(22) Filed: Jun. 2, 2016

(65) Prior Publication Data

US 2016/0274142 A1 Sep. 22, 2016

Related U.S. Application Data

(63) Continuation of application No. 13/898,519, filed on May 21, 2013, now Pat. No. 9,366,692.

(51) Int. Cl.
*G01N 3/08* (2006.01)
*G01P 21/02* (2006.01)
*G01N 3/62* (2006.01)

(52) U.S. Cl.
CPC ............... *G01P 21/02* (2013.01); *G01N 3/08* (2013.01); *G01N 3/62* (2013.01); *G01N 2203/021* (2013.01)

(58) Field of Classification Search
CPC ............ G01P 21/02; G01N 3/08; G01N 3/62
See application file for complete search history.

(56) References Cited

U.S. PATENT DOCUMENTS

| 4,991,446 | A | 2/1991 | Bechtel |
| 5,440,935 | A | 8/1995 | Petersen |
| 6,298,709 | B1 | 10/2001 | Artzner et al. |
| 6,597,145 | B1 | 7/2003 | Maresca et al. |
| 6,940,248 | B2 | 9/2005 | Maresca et al. |
| 9,658,122 | B2 * | 5/2017 | Saari ...................... G01L 1/26 |

(Continued)

FOREIGN PATENT DOCUMENTS

WO 9421991 A1 9/1994

OTHER PUBLICATIONS

International Search Report and Written Opinion in related international patent application No. PCT/US14/37114.

(Continued)

*Primary Examiner* — Bryan Bui
(74) *Attorney, Agent, or Firm* — Womble Bond Dickinson (US) LLP; Deborah M. Vernon; Heath T. Misley

(57) ABSTRACT

In a mechanical test system, a method of compensating for acceleration induced load error in a load sensor in a mechanical communication with a component comprises measuring an acceleration of the component to obtain an acceleration measurement. A load sensor measures a force applied by the mechanical test system to a test sample in substantially a same direction of the acceleration to obtain a force measurement. The force measurement is modified with a transfer function that includes at least one of a gain correction and a phase correction to compensate for an error value in the force measurement attributed to movement of at least the load sensor when the force is applied to the test sample.

18 Claims, 8 Drawing Sheets

(56) References Cited

U.S. PATENT DOCUMENTS

2005/0267695 A1 12/2005 German
2006/0070424 A1 4/2006 Saari et al.
2013/0305840 A1 11/2013 Saari et al.

OTHER PUBLICATIONS

International Preliminary Report on Patentability in related international patent application No. PCT/US14/37114, dated Nov. 24, 2015; 12 pages.
Invitation to Pay Additional Fees and Partial International Search Report in related international patent application No. PCT/US14/37114, dated Aug. 13, 2014; 6 pages.

* cited by examiner

ACCELERATION COMPENSATION OF LOAD SENSORS

CROSS-REFERENCE TO RELATED APPLICATION

This application is a continuation of U.S. patent application Ser. No. 13/898,519 filed May 21, 2013, now U.S. Pat. No. 9,366,692, the entire contents of which is incorporated herein by reference.

FIELD OF THE INVENTION

The invention relates generally to testing techniques for the characterization of materials. More specifically, the invention relates to the characterization and compensation of motion induced load errors in dynamic material testing machines.

BACKGROUND

Mechanical test systems are used to determine various characteristics of materials. For example tensile strength, amongst other parameters, is tested with systems such as the ElectroForce® 3200 Test Instrument from Bose Corporation. A linear electromagnetic motor is used to apply the load to the material. A sensor (e.g. a load cell) measures an output of the system while the material is under the load and provides a feedback signal, which is used in controlling operation of the motor. Relatively high-frequency resonances and phase delay introduced into the sensor by the system, the material being tested, or inherent in the sensor itself, can cause the feedback signal to negatively impact the operation of the motor. Furthermore, motions of the system can induce errors in the load measurement. Methods have been developed (e.g. American Society for Testing and Materials, ASTM E467) for the assessment and correction of these errors, however, these methods can be time consuming to implement. In some cases, they may not be practical or even possible (e.g. placing strain gauges on a biological sample).

U.S. Pat. No. 6,940,248 discloses a motion controller including a combining network having an acceleration input for receiving an acceleration signal representative of acceleration of a movable element and a position input for receiving a position signal representative of position of the movable element and an output for providing an inferred position signal representative of an inferred position of the movable element. The network includes a first signal processor for processing the acceleration signal to provide modified acceleration signal, a second signal processor for processing the position signal to provide a modified position signal and a combiner for combining the modified acceleration signal with the modified position signal to provide the inferred position signal. This system uses a combination of position detection and acceleration to generate a position source but does not teach a solution to reducing the error in a force measurement due to motion of the test system, high-frequency resonances or phase delay introduced into the sensor. Thus, there remains a requirement to reduce these error sources in an efficient manner.

BRIEF SUMMARY

All examples and features mentioned below can be combined in any technically possible way. In one aspect, in a mechanical test system, a method of compensating for acceleration induced load error in a load sensor in mechanical communication with a component includes measuring an acceleration of the component to obtain an acceleration measurement. The load sensor measures a force applied by the mechanical test system to a test sample in substantially a same direction of the acceleration, to obtain a force measurement. The force measurement is modified with a transfer function that includes at least one of a gain correction and a constant phase delay filter to compensate for an error value in the force measurement attributed to movement of at least the load sensor when the force is applied to the test sample.

Embodiments may include one of following features or any combination thereof. At least one waveform is mechanically applied to the test sample. A plurality of acceleration measurements and a plurality of force measurements for each waveform are recorded for a period of time. For each waveform, the plurality of acceleration measurements are converted with a Fourier Transform to create an acceleration frequency response. For each waveform, the plurality of force measurements are converted with a Fourier Transform to create a force frequency response. An input gain and an input phase are determined for each acceleration frequency response of each waveform. An output gain and an output phase are determined for each force frequency response of each waveform. For each waveform, a fundamental gain is determined by dividing the output gain by the input gain. For each waveform, a phase difference is determined by subtracting the input phase from the output phase. The fundamental gain is averaged from each waveform to determine a gain correction. The phase difference is converted into a constant phase delay filter. Substantially half of a mass of the test sample is attached to the mechanical test system while the transfer function is determined. Substantially half of a mass of the test sample is recorded while the transfer function is determined. The at least one waveform includes three monotone waveforms. For each of the three monotone waveforms, an excitation amplitude is ramped to a desired amplitude. The plurality of acceleration measurements and the plurality of force measurements are recorded for the period of time. The excitation amplitude is decreased until the force measurement is substantially zero. Measuring with a Fourier Transform includes measuring with a Discrete Fourier Transform. The period of time is at least two seconds. Applying at least one waveform includes applying three monotone waveforms. The acceleration measurement is filtered with a High Pass Filter (HPF). Filtering with the HPF includes filtering with a Butterworth filter. A second acceleration of a second component is measured to obtain a second acceleration measurement. The second component is in mechanical communication with the load sensor. The second component is part of the mechanical test system.

In another aspect, an apparatus to compensate for acceleration induced load error in a load sensor includes a movement detector in mechanical communication with a component of a mechanical test system. The movement detector is configured to measure an acceleration of the component to obtain an acceleration measurement. A load sensor is in mechanical communication with the component. The load sensor is configured to measure a force applied by the mechanical test system to a test sample in substantially a same direction of the acceleration to obtain a force measurement. A processor is configured to modify the force measurement with a transfer function that includes at least one of a gain correction and a constant phase delay filter to compensate for an error value in the force measurement attributed to movement of at least the load sensor when the force is applied to the test sample.

Embodiments may include one of the above and/or below features, or any combination thereof. The movement detector is an accelerometer. The movement detector is a displacement sensor and the processor computes a second derivative of the movement output. The displacement sensor is proximately located to an actuator on the mechanical test system. The actuator includes a motor that communicates the force to the test sample. The displacement sensor is proximately located to the load sensor. The force is substantially collinear with the longest dimension of the test sample. The force is substantially torsional around the longest dimension of the test sample.

In another aspect, a method of compensating for acceleration induced load error in a load sensor in mechanical communication with a component includes measuring an acceleration of a component to obtain an acceleration measurement. The load sensor measures a force applied to a test sample in substantially a same direction as a measurable portion of the acceleration to obtain a force measurement. The force measurement is modified with a transfer function that includes at least one of a gain correction and a phase correction to compensate for an error value in the force measurement attributed to movement of at lest the load sensor when the force is applied to the test sample. The transfer function is determined by mechanically applying at least one waveform to the test sample. A plurality of acceleration measurements and a plurality of force measurements for each waveform are recorded for a period of time. For each waveform, the plurality of acceleration measurements are converted with a Fourier Transform to create an acceleration frequency response. For each waveform, the plurality of force measurements are converted with a Fourier Transform to create a force frequency response. An input gain and an input phase are determined for each acceleration frequency response of each waveform. An output gain and an output phase are determined for each force frequency response of each waveform. For each waveform, a fundamental gain is determined by dividing the output gain by the input gain. For each waveform, a phase difference is determined by subtracting the input phase from the output phase. The fundamental gain from each waveform is converted into a gain correction. The gain correction has a variable gain as a function of frequency. The phase difference from each waveform is converted into a phase correction. The phase correction has a variable phase delay as a function of frequency.

Embodiments may include one of the above and/or below features, or any combination thereof. The acceleration is an angular acceleration including a measureable portion of an axial acceleration being substantially in a same direction as an axial force when the axial force is applied to the test sample. A measurable portion of a torsional acceleration is substantially in a same direction as a torsional force when the torsional force is applied to the test sample.

BRIEF DESCRIPTION OF THE SEVERAL VIEWS OF THE DRAWINGS

The above and further advantages of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

DETAILED DESCRIPTION

Embodiments of methods and systems described herein provide for the characterization and compensation of errors in sensors used to measure forces applied to a test sample. Non-limiting examples of error sources include errors due to movement of the sensor during test, high-frequency resonances between the sensor and various components in the test system and phase delays between the force applied to the test sample and the force measured by the sensor. In addition, there are delays between the sensor and other measurement devices used to determine sensor errors (e.g. a separate accelerometer).

Figure 1:
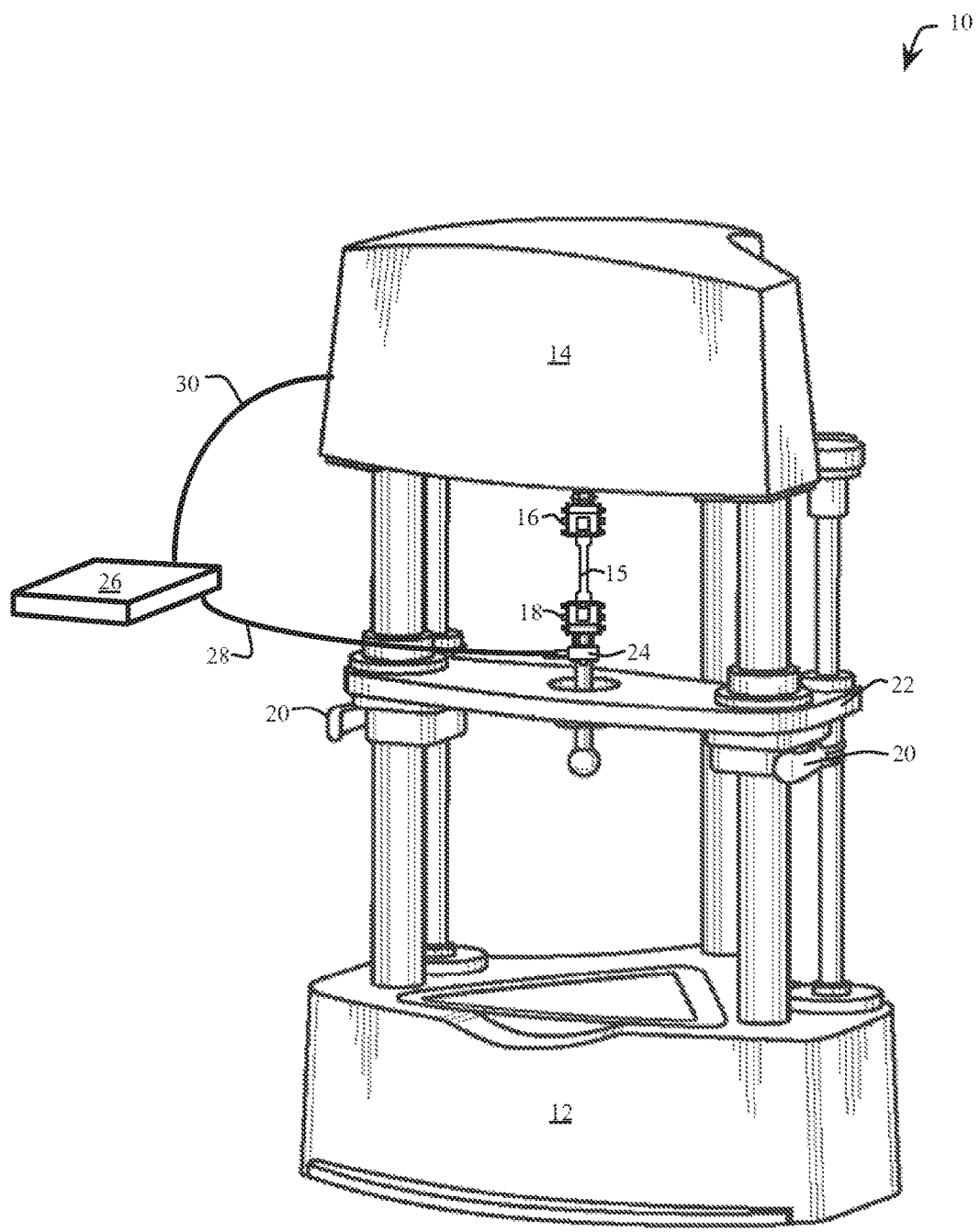
FIG. 1 is perspective view of a mechanical test system.

Referring to FIG. 1, a system 10 for applying a load to a test sample 15 (e.g. a sample of material) includes a lower housing 12 and an upper housing 14. An actuator 13 (not shown) in the form of a linear electro-magnetic motor (not shown) is contained within the upper housing 14. The test sample 15 is placed between an upper sample grip 16 and a lower sample grip 18. The distance between the grips is adjusted to secure the material between the grips. This is achieved by opening a pair of clamps 20, raising or lowering a stage 22 to which the lower grip 18 is secured, and then closing the clamps 20. Depending on the material type, different types of grips can be used to secure the test sample 15. The motor can move the upper grip 16 (e.g. up and down) to apply an axial load to the material secured between the grips. The lower grip 18 is secured in a stationary position when the load is being applied to the test sample 15. Various types of loads such as compression, tension, torque, bending, etc. are applied to the material depending in various embodiments of the system 10. Various types of test samples are tested, including biological samples and metals for example.

A load sensor 24 (e.g. a load cell) measures an output of the system 10 (which can include a characteristic of the material) while the load is being applied to the test sample 15 through the sample grips 16 and 18. Various types of sensors can be used to measure a number of different outputs of the system such as load, displacement, strain, stress, velocity, acceleration, pressure, torque, rotation etc. A processor 26 is part of and controls the operation of the system 10. The processor is connected to the load sensor 24 and the system 10 (to control the motor) by respective data buses 28 and 30. In a preferred embodiment, electrical power to the system 10 is provided by AC mains. The power to some or all of the system 10 may be conditioned by a power supply and a transformer.

Figure 2A:
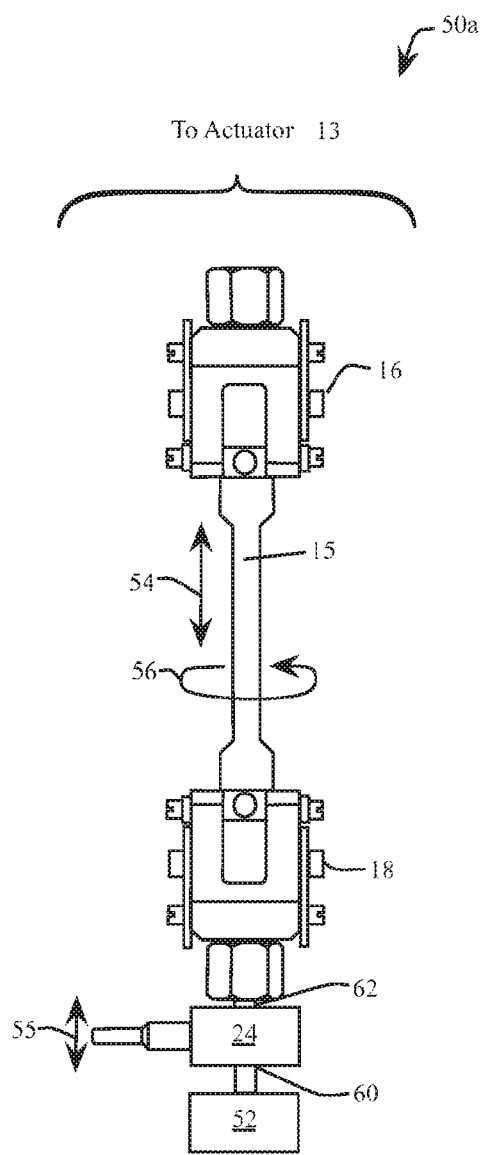
FIG. 2A is side view of a mounted test sample showing a placement of the load sensor and accelerometer.

FIG. 2A illustrates a test sample 15 secured by an upper sample grip 16 and a lower sample grip 18. The upper sample grip 16 communicates with the actuator 13. In one embodiment, a load sensor 24 is attached to the lower sample grip 18 in proximity to an accelerometer 52 attached to the stage 22. During test the actuator 13 imparts a force on the sample 15, for example a tensile or axial force causing a linear displacement 54 or a torsional force causing a rotational displacement 56. In other embodiments, the force is compressive, or torsional with a direction of rotation opposite that depicted in FIG. 2A. It is envisioned that other embodiments will impart other force directions, not limited to axial or torsional forces. In the example where an axial force is applied to the test sample 15, the load sensor 24 used to measure the force will also experience a linear displacement 55 typically of lesser magnitude than that experience by the test sample 15, but large enough to cause a significant measurement error of the force applied to the test sample 15. The load sensor 24 will have a force measurement error due to the mass attached to the load cell multiplied by the acceleration. The acceleration is a function of the amplitude and frequency of the waveform applied by the actuator 13. To a lesser extent, the mechanical stiffness of system and the sample also determine the error in the force measurement. FIG. 2A also shows a placement of the accelerometer 52 attached to the stage 22 or frame of the test system 10. Alternative placements of the accelerometer 52 are adjacent to the load sensor 24 at a passive side location 60 or adjacent to the load sensor 24 at an active side location 62, the active side being on the same side of the load sensor 24 as the test sample 15. The accelerometer 52 is able to provide better compensation for load errors when placed at location 62, compared to 60 and 60 compared to being mounted on the stage 22.

Figure 2B:
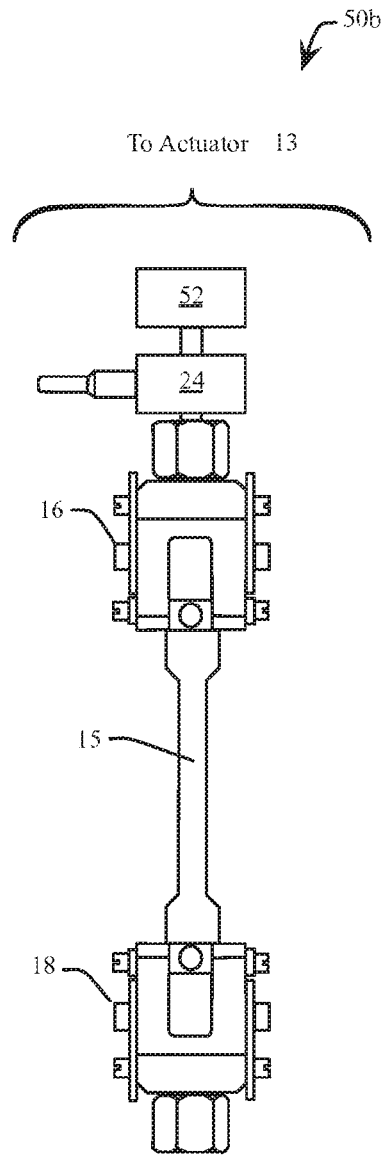
FIG. 2B is side view of a mounted test sample showing a preferred placement of the load sensor and accelerometer.

FIG. 2B shows a preferred embodiment with the load sensor 24 attached to the upper sample grip 16 and the accelerometer 52 on the passive side of the load sensor 24 in proximity to the actuator 13. Advantageously, this enables the test sample 15 to be submersed in a bath during testing or for heavy or asymmetrical fixtures to be used and mounted on the frame of the mechanical test system 10. However, the embodiment 50b shown in FIG. 2B significantly increases the error in force measurement compared to the embodiment 50a shown in FIG. 2A. For example, a sine wave excitation of +/−1 mm at 100 Hz with a 100 gram fixture produces a load sensor error of 39.5N.

The present disclosure provides a solution to this increased force error term by measuring the acceleration-induced error from the measured load, creating appropriate compensation factors or filters and substantially removing the error term from the measured load.

Figure 3:
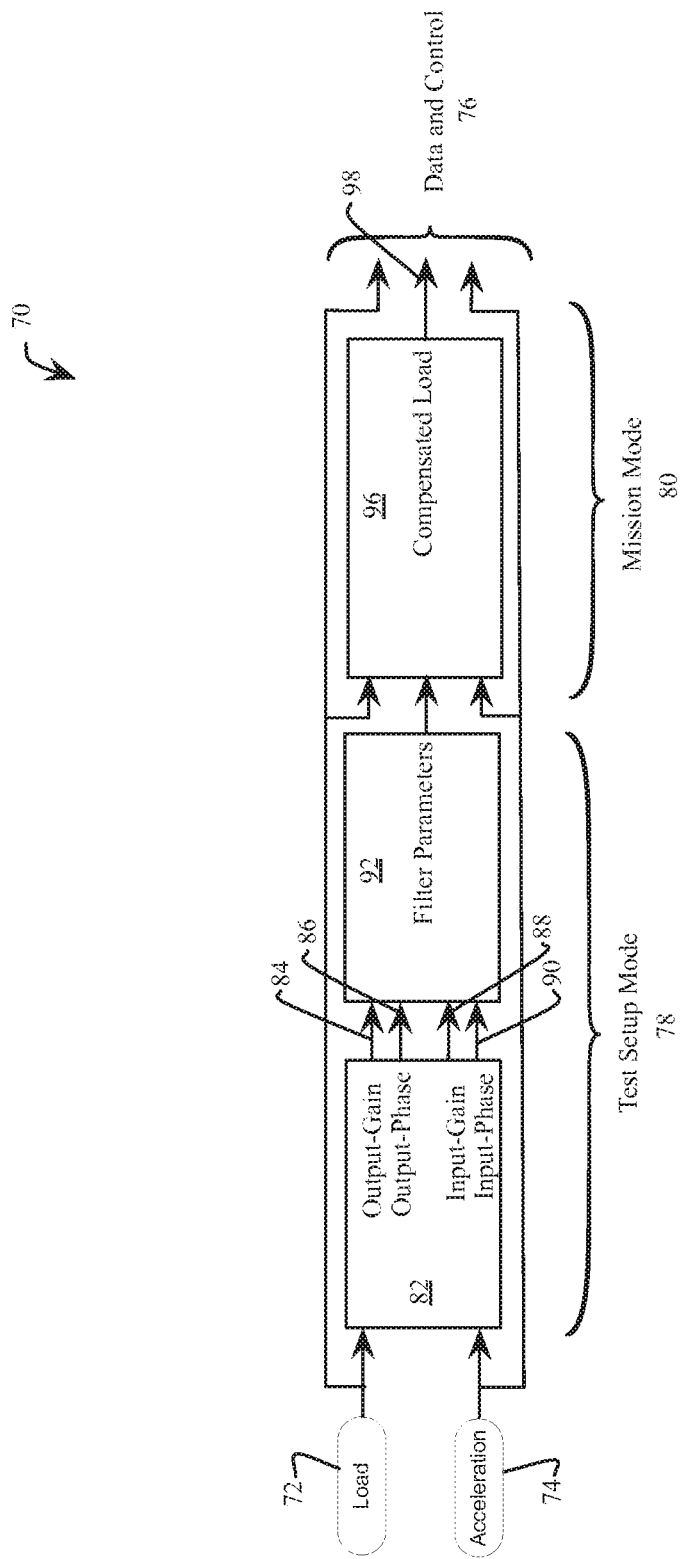
FIG. 3 is block diagram of an automated compensation scheme.

With reference to FIG. 3, the load 72 measured by the load sensor 24 and the acceleration 74 measured by the accelerometer 52 are input to an automated compensation system 70, which produces outputs 76 used for data analysis and control of the actuator 13. The outputs 76 include the uncompensated load 72 and acceleration 74 values as well as a compensated load channel 98 that corrects for gain and phase errors between the force applied to the test sample 15 and the force measured by the load sensor 24. The system 70 includes two functional blocks 82 and 92 used during a Test Setup Mode 78 and a functional block 96 used during a Mission Mode 80 (e.g. the mode where an intact test sample 15 is characterized).

During Test Setup Mode 78 a half-mass characterization is performed, where a mass representing half of the mass of the test sample 15 is attached to the upper sample grip 16 but not connected to the lower sample grip 18. In certain circumstances where it is not practical to mount a half sample to the upper sample grip 16, a measured sample mass is input into the computation by the user. For example, biological samples or purely compression tests are challenging to perform because of the impracticality of cutting a sample in half During the Test Setup Mode 78 a dynamic load error is determined and converted to gain and phase compensation. The dynamic load error represents the effective mass supported by the load sensor 24 as:

$$Me = Ms/2 + Mf$$

where Me is the effective mass, Ms/2 is half the sample mass and Mf is the fixture mass (e.g. one of the sample grips).

Functional block 82 applies a mechanical force to the test sample 15 and samples the load 72 and the acceleration 74. In a preferred embodiment, the applied force is three sinusoidal excitations applied in succession. This disclosure envisions other waveforms that are not monotone although preferentially a monotone waveform reduces in-band harmonics that would reduce the accuracy of the error estimate. This disclosure also envisions different numbers of applied waveforms. A single waveform will suffice if the gain and phase errors are relatively uniform over a wide frequency range. More than three waveforms will provide a more accurate error estimate but at the expense of increased test setup duration. Each combination of fixtures and test samples will have a separate execution of the Test Setup Mode 78. For example, a test system 10 with an actuator 13 that exerts 225 Newtons of force (e.g. 225 N LM1 model) will use characterization waveforms with fundamental frequencies of 75 Hz, 125 Hz and 200 Hz, while a higher performance model (eg. 7500 N LM3) will use frequencies of 15 Hz, 20 Hz and 25 Hz. The frequencies are chosen to be above the mass spring resonance of the actuator 13 in free air. Preferentially, the accelerometer measurements are filtered with a high pass filter. In a preferred embodiment, the filter is a first order Butterworth Filter with a 3 dB roll-off point of 1 Hz.

A bias force is applied to the test sample 15 until the force measured by the load sensor 24 is substantially zero. The monotone waveform is then ramped until the excitation amplitude reaches a desired amplitude. The waveform is then applied for a period of time (e.g. two seconds in one embodiment), while sampling load 72 and acceleration 74 values. In one example a 5 KHz sample rate is used to generate 10,000 samples for load 72 and 10,000 samples for acceleration 74. The excitation amplitude of the waveform is then decreased until the force measured by the load sensor 24 is substantially zero. This sequence repeats for the subsequent waveforms.

After the excitation waveforms are applied, the time samples of the load 72 and acceleration 74 are converted to the frequency domain by a Fourier Transform. The Fourier Transform is preferentially a Discrete Fourier Transform although other transforms are envisioned, for example a Fast Fourier Transform. An Output-Gain 84 and Output-Phase 86 are calculated from the frequency domain version of sampled load 72 measurements. An Input-Gain 88 and Input-Phase 90 are calculated from the frequency domain version of sampled acceleration 74 measurements.

The functional block 92 takes the Output-Gain 84, Output-Phase 86, Input-Gain 88 and Input-Phase 90 values from the functional block 82 and determines a gain correction and phase correction to substantially compensate for the error in the force measurement due to the displacement of the load sensor 24 during Mission Mode 80. The gain compensation is determined by dividing the Output-Gain 84 by the Input-Gain 88 for each of the applied waveforms. In one embodiment, using three applied waveforms, the three gain compensation values are averaged to produce a single gain compensation to be used during Mission Mode 80. In another embodiment, a transfer function of gain correction amplitude as a function of frequency is created and applied during Mission Mode 80. A gain compensation transfer function is appropriately used when the gain correction varies significantly over the useable frequency range of the mechanical test system 10.

To calculate the phase correction the phase differential is calculated by subtracting the Input-Phase 90 from the Output-Phase 86 to create a phase differential. The phase differential is then converted to a time delay. The time delay value for each applied waveform is then converted to a phase correction, preferentially a constant phase delay filter. In one embodiment, the constant phase delay filter is created using the Thiran function in MATLAB®. Based on the magnitude of the phase delay, either the load 72 channel or the acceleration 74 channel will be delayed to synchronize the two.

The following is a non-limiting example of pseudo-code used to generate the estimates for gain compensation and phase compensation, including the generation of phase and gain for both the load and acceleration measurements as well as gain correction and phase delay filtering of the sensor 24. Where parameters are provided they are ones that have been shown to work well in some simulations, but may vary with the application, and other combinations of parameters are envisioned. MATLAB® style conventions are primarily used in this example, however other programming styles are also envisioned.

Calculation of Gain and Phase Estimates for Load and Acceleration:

```
function [fundgain fundphase conf] = AccelComp_DFT2( freq , acceldata , loaddata , Fs )
% function [fundgain fundphase conf] = AccelComp_DFT2( freq , acceldata , loaddata , Fs )
% Input
% freq: scalar frequency of the input and output data
% input: vector of input data
% output: vector of output data
% Fs: Sample Rate
%
% Output
% fundgain: gain at the fundamental frequency between input and output
% fundphase: phase at the fundamental frequency between input and output
% conf: Confidence (max=1, min=0) of the result. Based upon error after
%        compensation is used
%
% Typical function call
% [mass_eff mass_eff_phase conf] = AccelComp_DFT( currfreq , acceldata , loaddata , Fs );
%
Ni = length( acceldata );
No = length( loaddata );
if Ni ~= No
    error( 'Input and Output must be of the same length' )
else
    N = Ni;
    clear Ni No
end
% define number of harmonics for testing total harmonic distortion
NumHarmonics = 9;
t = [1:N]'/Fs;
% Optional Windowing of the inputs
if 0
    win = hamming(N);
    acceldata = win.*acceldata;
    loaddata = win.*loaddata;
end
% Pre-allocate memory for gain and phase data
out_gain = zeros(NumHarmonics+1,1);
in_gain = zeros(NumHarmonics+1,1);
out_phase = zeros(NumHarmonics+1,1);
in_phase = zeros(NumHarmonics+1,1);
for idx = 1 : (NumHarmonics+1)
    %Calculate Magnitude and Phase
    y_sin = sin( freq*idx * 2*pi*t ); % Ideal SINE at this freq
    y_cos = cos( freq*idx * 2*pi*t ); % Ideal SINE at this freq
    Bc = sum( loaddata .* y_cos ); % Calculation of cosine term
    Bs = sum( loaddata .* y_sin ); % Calculation of sine term
    out_gain(idx) = sqrt (Bc^2+Bs^2); % Amplitude of OUTPUT at this frequency
    out_phase(idx) = 180/pi * atan2(Bc,Bs); % Phase of OUTPUT at this
```

-continued

```
frequency [degrees]
      Ac = sum( acceldata .* y_cos ); % Calculation of cosine term
      As = sum( acceldata .* y_sin ); % Calculation of sine term
      in_gain(idx) = sqrt(Ac^2+As^2); % Amplitude of INPUT at this frequency
      in_phase(idx) = 180/pi * atan2(Ac,As); % Phase of INPUT at this frequency
[degrees]
end
% Calculation of the fundamental frequency gain and phase
fundgain = out_gain(1) / in_gain(1) ; % Gain between INPUT and OUTPUT
fundphase = out_phase(1) – in_phase(1); % Difference in phase (INPUT->OUTPUT)
[degrees]
% Adjust phase to be in range of [-180 , 180]
fundphase = fundphase – (fundphase>180)*360 + (fundphase<–180)*360;
% Calculation of the confidence interval
% The second calculation is based upon reduced error in the load
% calculation (assuming 0 is the desired sample load). This calculation is
% sensitive to phase issues between input and output but not strong
% harmonics that have a similar gain to the fundamental.
loaddatap = loaddata–mean(loaddata);
acceldatap = acceldata–mean(acceldata);
comploaderrordatap = loaddatap – acceldatap * fundgain;
% Take ratio of RMS, verify that it is in the range of 0 to 1 with 1 being
% the highest confidence
conf = 1 – min( sqrt(mean(comploaderrordatap.^2)) / sqrt(mean(loaddatap.^2))
,1 );
```

Calculation of the Phase Differential and Phase Filter:

```
for j = 1:length(fundphase) %phase at each frequency
        tauL(j) = (abs(fundphase(j)/360))*(1/acmt.accel_comp_freq(j));
end
systau = thiran(tauL(end),1/Fs); %generate system transfer function using
thiran function (constant phase delay)
%If maximum phase is less than +/-X degrees, then no delay
      c = zeros(1,length(fundphase));
      for j = 1:length(fundphase)
            if abs(fundphase(j)) > 5
                  c(j) = 1;
            end
      end
      if sum (c)>=1
            if fundphase(end)>acmt.phasefactor
                  %delay load channel
                  sysload = sysload*systau;
                  [num_load den_load] = tfdata(sysload,'v ');
                  tau = tauL(end);
            else
                  %delay acceleration
                  sysacc = sysacc*systau;
                  [num_acc den_acc] = tfdata(sysacc,'v ');
                  tau = –tauL(end);
            end
      else
            tau = 0;
      end
```

Figure 4:
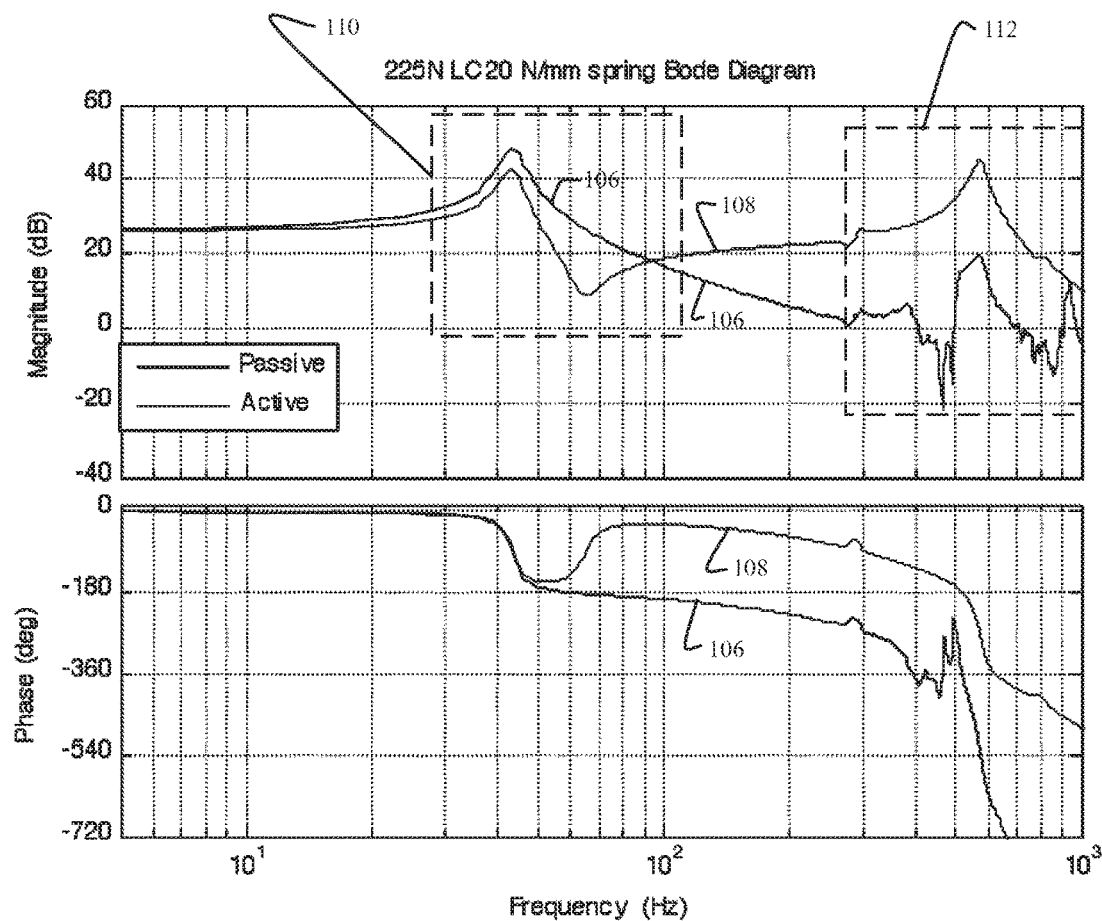
FIG. 4 is graphical view of a Bode diagram showing an open loop load response of the system.

FIG. 4 shows the frequency response of uncompensated load 72 and acceleration 74 measurements for an ELF 3220 mechanical test system, a 20N/mm load sensor 24 proximately located by the actuator 13. Notably, the gain and phase errors vary significantly depending on whether the acceleration is measured on the passive side 106 of the load sensor 24 (e.g. between the load sensor 24 and actuator 13) or on the active side 108 of the load sensor 24 (e.g. between the load sensor 24 and the test sample 15). Significant errors are also present due to reasonance. FIG. 4 shows a resonance 112 at 550 Hz between the fixtures (e.g. sample grips 16 and 18) and the load sensor 24, and a primary resonance 110 at 45 hz due to the mechanical test system 10—specifically due to the mass of the moving part of the motor (e.g. actuator 13) and the sample grip 16 attached to the motor.

In a preferred embodiment, the accelerometer 52 is a displacement sensor that measures displacement and the acceleration value 74 is derived by taking the second derivative of the displacement measured by the displacement sensor, preferably with a high resolution, low noise and low latency signal processor. The displacement sensor provides similar accuracy to traditional accelerometers, (with the advantage of system simplification), which when combined with the automated compensation system 70, allows the accelerometer 52 to be placed close to the actuator 13 (shown in FIG. 2B), on the stage 22 or at locations 60 or 62 (as shown in FIG. 2A), while maintaining acceptable error compensation.

Figure 5:
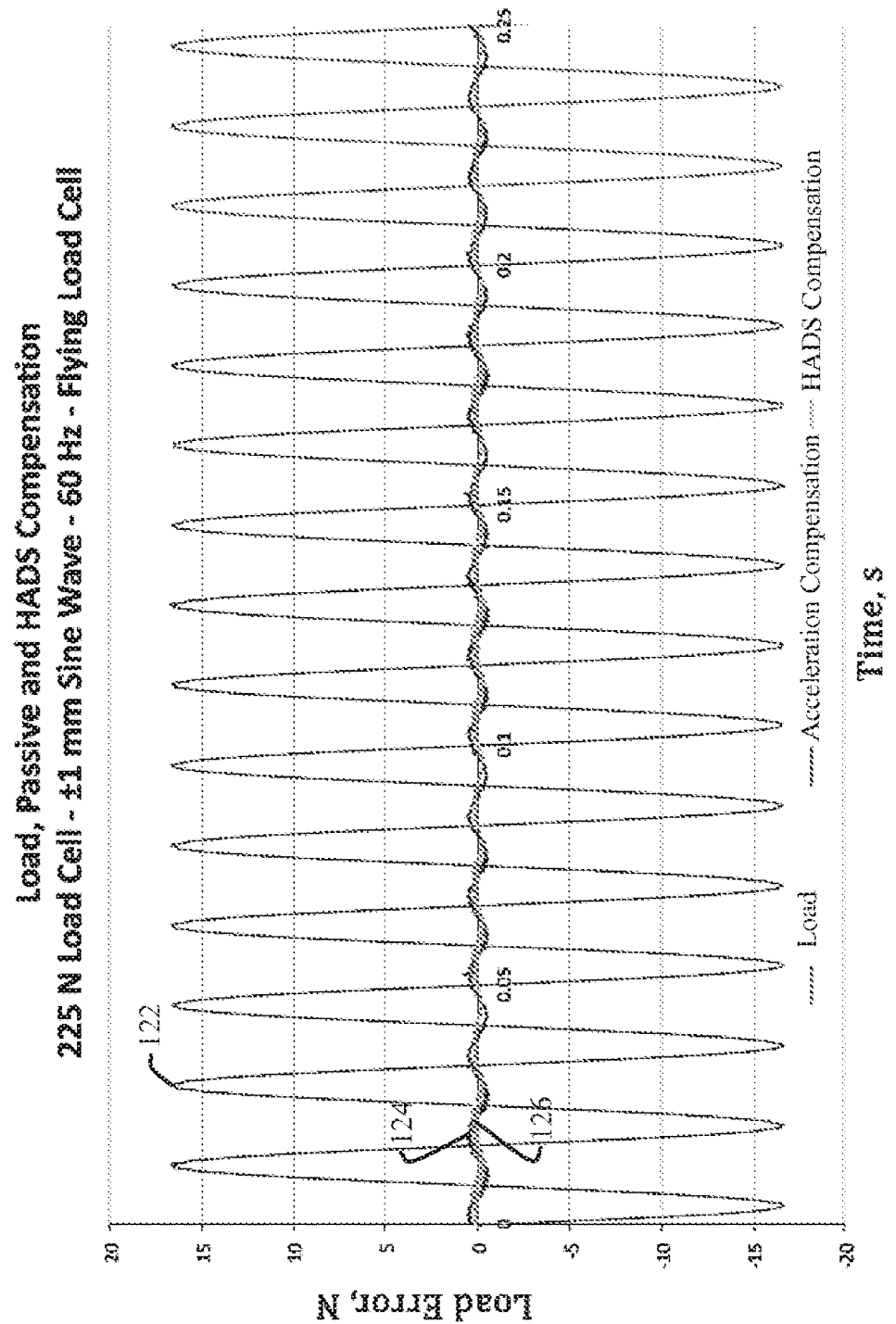
FIG. 5 is graphical view of a load error reduction.

FIG. 5 illustrates the efficacy of the automated compensation system 70 with acceleration measured by a traditional accelerometer based on a variable capacitance design compared to a measurement with a displacement sensor. The error in the uncompensated load 122 is significantly reduced as shown by the accelerometer results 124 and the displacement sensor results 126. The compensated load 126 (also shown as 98 in FIG. 3), using the second derivative of a displacement sensor, shows a significant reduction in variation, comparable to that achieved by the accelerometer but with the advantages of reduced cabling, weight and system components.

Figure 6A:
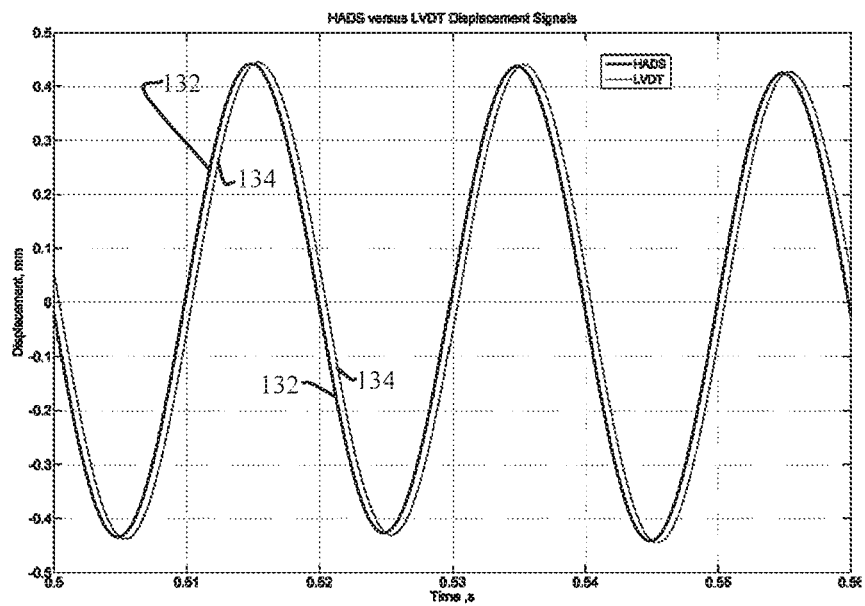
FIG. 6A is graphical view comparing a displacement response of a High Accuracy Displacement Sensor (HADS), which is a displacement sensor manufactured by Bose Corp., to a Linear Variable Displacement Transformer (LVDT).
Figure 6B:
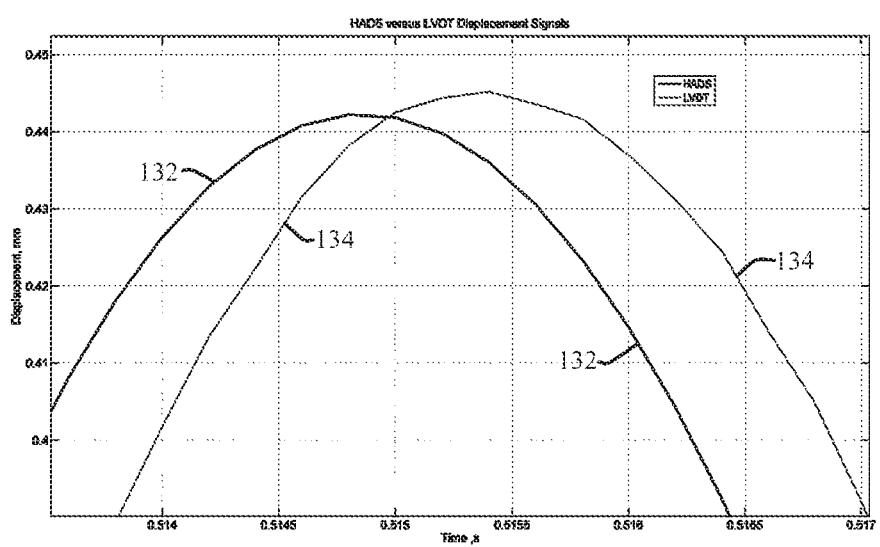
FIG. 6B is graphical view of FIG. 6A showing detail of a peak response.
Figure 7A:
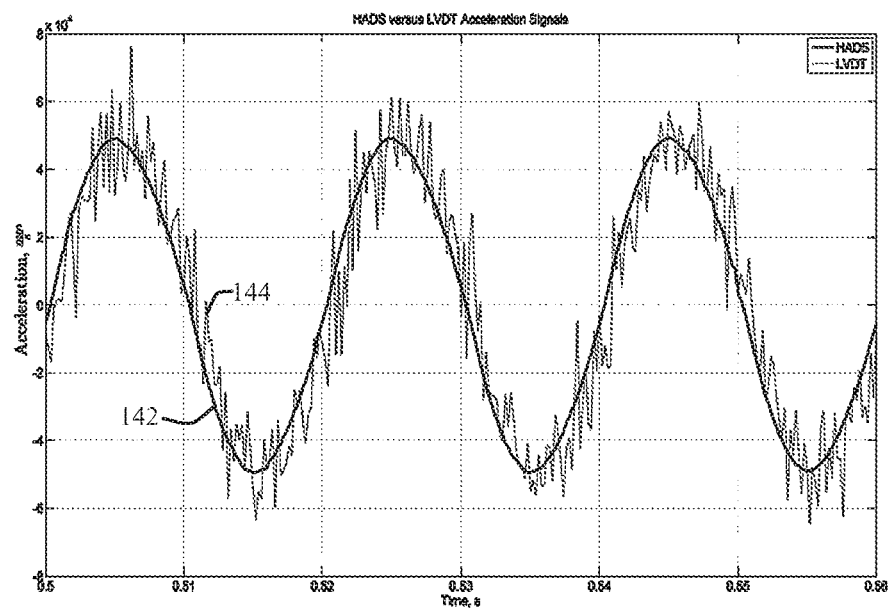
FIG. 7A is graphical view comparing an acceleration response of the HADS to the LVDT.
Figure 7B:
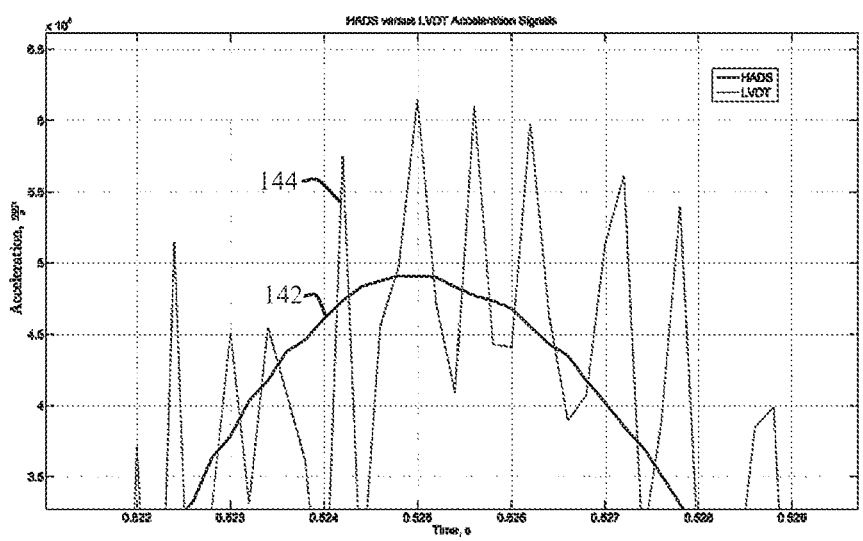
FIG. 7B is graphical view of FIG. 7A showing detail of a peak response.

FIG. 6A and FIG. 6B compare the measured displacement with a HADS 132 to that measured by an instrument grade LVDT 134. FIG. 7A and FIG. 7B compare the derived acceleration with a HADS 142 to that derived by an instrument grade LVDT 144. The HADS provides a significantly improved resolution and noise performance. Specifically, the total harmonic noise plus the background noise floor (THD+N) of the HADS based acceleration value only increased 13% compared to the LVDT based acceleration value of approximately 1,000%. This increase in THD+N is due to the nature of the processing required to compute the second derivative of the displacement signal.

Figure 8:
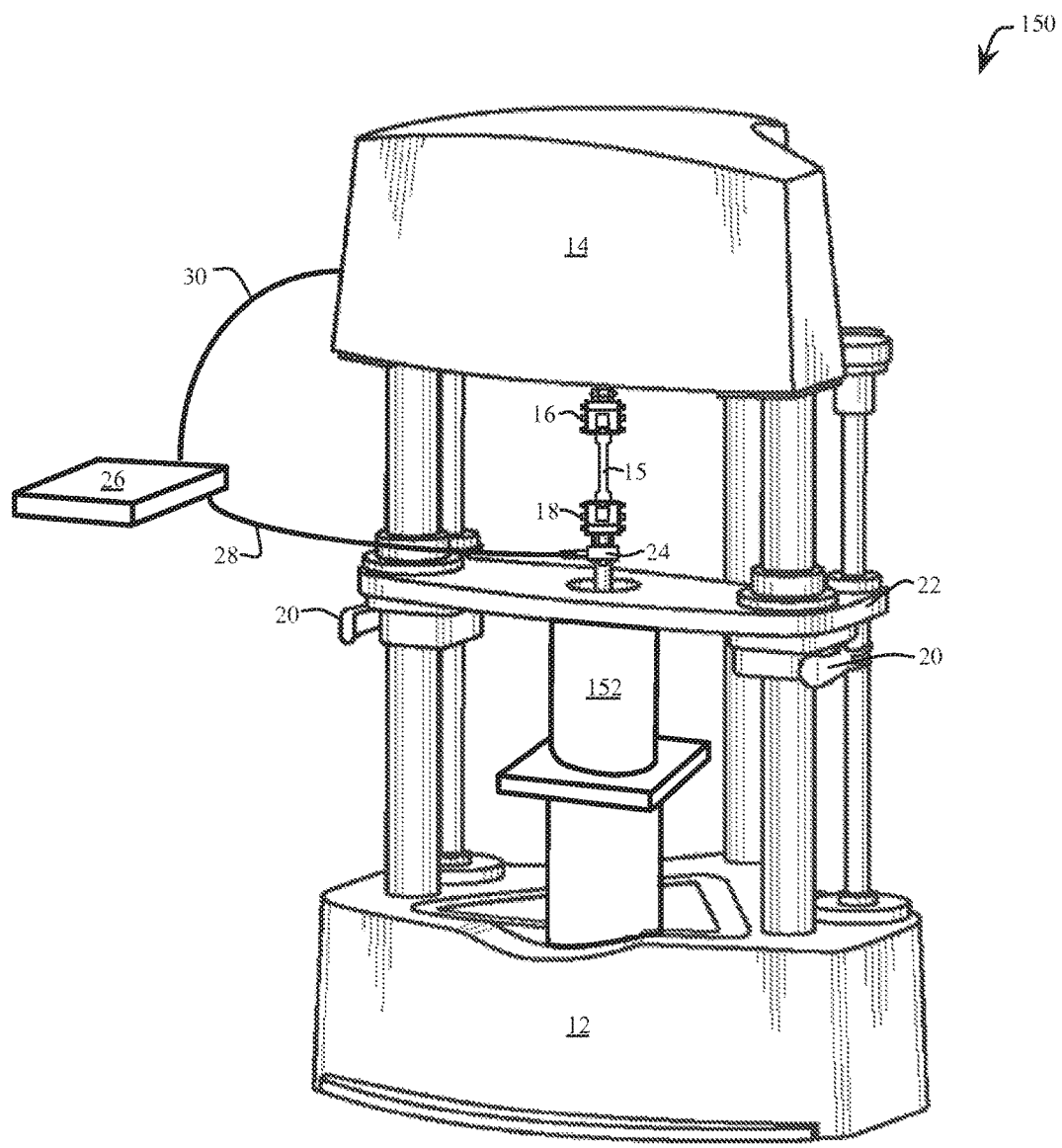
FIG. 8 is perspective view of a mechanical test system capable of imparting axial and torsional forces to a test sample.

FIG. 8 extends the embodiment of the mechanical test system 10 shown in FIG. 1 and the teachings described above to include a test system 150 that can impart axial and torsional forces to the test sample 15 either individually or in combination. In the embodiment 150, an axial force is applied to the test 15 with the actuator 13 (not shown) and a torsional force is applied with a second actuator 152. The load sensor 24 shown in FIG. 8 is an axial-torsional sensor when used with the embodiment 150, capable of simultaneously measuring both axial and torsional forces and an angular acceleration, with a measurable component being aligned to the axial force and a measurable component being aligned to the torsional force. The rotational displacement signal is currently measured within the torsional actuator 152. In other embodiments, the rotational acceleration is measured by a sensor in proximity to the torsional load sensor.

Certain embodiments of the systems and methods described above comprise computer components and computer-implemented steps that will be apparent to those skilled in the art. For example, it should be understood by one of skill in the art that the computer-implemented steps may be stored as computer-executable instructions on a computer-readable medium such as, for example, floppy disks, hard disks, optical disks, Flash ROMS, nonvolatile ROM, and RAM. Furthermore, it should be understood by one of skill in the art that the computer-executable instructions may be executed on a variety of processors such as, for example, microprocessors, digital signal processors, gate arrays, etc. For ease of exposition, not every step or element of the systems and methods described above is described herein as part of a computer system, but those skilled in the art will recognize that each step or element may have a corresponding computer system or software component. Such computer system and/or software components are therefore enabled by describing their corresponding steps or elements (that is, their functionality), and are within the scope of the disclosure.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wire-line, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

A number of implementations have been described. Nevertheless, it will be understood that additional modifications may be made without departing from the scope of the inventive concepts described herein, and, accordingly, other embodiments are within the scope of the following claims:

What is claimed is:

1. An apparatus to compensate for acceleration induced load error in a load sensor, the apparatus comprising:
    a movement detector in mechanical communication with a component of a mechanical test system, the movement detector configured to measure an acceleration of the component in response to at least one waveform being applied to a test sample to obtain an acceleration measurement;
    a load sensor in mechanical communication with the component, the load sensor configured to measure a force applied by the mechanical test system in response to at least one waveform being applied to the test sample in substantially a same direction as the acceleration, to obtain a force measurement; and
    a processor configured to modify the force measurement with a transfer function that includes at least one of a gain correction and a phase delay filter to compensate for an error in the force measurement attributed to movement of at least the load sensor when the force is applied to the test sample, wherein the gain correction and phase delay filter are calculated based on a Fourier Transform of a plurality of acceleration measurements and a plurality of force measurements recorded for a period of time for at least one waveform applied to the test sample.

2. The apparatus of claim 1, wherein the processor is further configured to determine the transfer function by:
    applying at least one waveform to the test sample;
    recording for a period of time, a plurality of acceleration measurements and a plurality of force measurements for each waveform;
    converting, for each waveform, the plurality of acceleration measurements with a Fourier Transform to create an acceleration frequency response;
    converting, for each waveform, the plurality of force measurements with a Fourier Transform to create a force frequency response;
    determining, for each acceleration frequency response of each waveform, an input gain;
    determining, for each force frequency response of each waveform, an output gain;
    determining, for each waveform, a fundamental gain by dividing the output gain by the input gain; and
    averaging the fundamental gain from each waveform to determine a gain correction.

3. The apparatus of claim 1, wherein the processor is further configured to determine the transfer function by:
    applying at least one waveform to the test sample;
    recording for a period of time, a plurality of acceleration measurements and a plurality of force measurements for each waveform;
    converting, for each waveform, the plurality of acceleration measurements with a Fourier Transform to create an acceleration frequency response;
    converting, for each waveform, the plurality of force measurements with a Fourier Transform to create a force frequency response;
    determining, for each acceleration frequency response of each waveform, an input phase;
    determining, for each force frequency response of each waveform, an output phase;
    determining, for each waveform, a phase difference by subtracting the input phase from the output phase; and
    converting the phase difference into the phase delay filter.

4. The apparatus of claim 1, wherein the processor is further configured to determine the transfer function by:
    applying at least one waveform to the test sample;
    recording for a period of time, a plurality of acceleration measurements and a plurality of force measurements for each waveform;
    converting, for each waveform, the plurality of acceleration measurements with a Fourier Transform to create an acceleration frequency response;
    converting, for each waveform, the plurality of force measurements with a Fourier Transform to create a force frequency response;
    determining, for each acceleration frequency response of each waveform, an input gain and an input phase;
    determining, for each force frequency response of each waveform, an output gain and an output phase;
    averaging the fundamental gain from each waveform to determine a gain correction; and
    converting the phase difference into the phase delay filter.

5. The apparatus of claim 1, wherein the processor is further configured to attach substantially half of a mass of the test sample to the mechanical test system while the transfer function is determined.

6. The apparatus of claim 1, wherein the processor is further configured to record substantially half of a mass of the test sample while the transfer function is determined.

7. The apparatus of claim 1, wherein the at least one waveform includes three monotone waveforms; and the processor is further configured, for each of the three monotone waveforms, to ramp an excitation amplitude to a desired amplitude, record the plurality of acceleration measurements and the plurality of force measurements for the period of time, and decrease the excitation amplitude until the force measurement is substantially zero.

8. The apparatus of claim 1, wherein the Fourier Transform includes a Discrete Fourier Transform.

9. The apparatus of claim 1, wherein the period of time is at least two seconds.

10. The apparatus of claim 1, wherein the at least one waveform includes three monotone waveforms.

11. The apparatus of claim 1, wherein the processor is further configured to filter the acceleration measurement with a High Pass Filter (HPF).

12. The apparatus of claim 11, wherein filtering with the HPF includes filtering with a Butterworth filter.

13. The apparatus of claim 1, wherein the movement detector is further configured to measure a second acceleration of a second component to obtain a second acceleration measurement, the second component being in mechanical communication with the load sensor and being part of the mechanical test system.

14. An apparatus to compensate for acceleration induced load error in a load sensor, the apparatus comprising:
- a movement detector configured to measure an acceleration of the component to obtain an acceleration measurement;
- a load sensor configured to measure a force applied to a test sample in substantially a same direction as the acceleration, to obtain a force measurement; and
- a processor configured to modify the force measurement with a transfer function that includes at least one of a gain correction and a phase correction to compensate for an error value in the force measurement attributed to movement of at least the load sensor when the force is applied to the test sample, wherein the transfer function determined by:
  - mechanically applying at least one waveform to the test sample;
  - recording for a period of time, a plurality of acceleration measurements and a plurality of force measurements for each waveform;
  - converting, for each waveform, the plurality of acceleration measurements with a Fourier Transform to create an acceleration frequency response;
  - converting, for each waveform, the plurality of force measurements with a Fourier Transform to create a force frequency response;
  - determining, for each acceleration frequency response of each waveform, an input gain and an input phase;
  - determining, for each force frequency response of each waveform, an output gain and an output phase;
  - determining, for each waveform, a fundamental gain by dividing the output gain by the input gain;
  - determining, for each waveform, a phase difference by subtracting the input phase from the output phase;
  - converting the fundamental gain from each waveform into a gain correction, the gain correction having a variable gain as a function of frequency; and
  - converting the phase difference from each waveform into a phase correction, the phase correction having a variable phase delay as a function of frequency.

15. The apparatus of claim 14, wherein the acceleration is an angular acceleration including a measurable portion of an axial acceleration being substantially in a same direction as an axial force when the axial force is applied to the test sample and a measurable portion of a torsional acceleration being substantially in a same direction as a torsional force when the torsional force is applied to the test sample.

16. The apparatus of claim 14, wherein the processor is further configured to attach substantially half of a mass of the test sample to the mechanical test system while the transfer function is determined.

17. The apparatus of claim 14, wherein the processor is further configured to record substantially half of a mass of the test sample while the transfer function is determined.

18. The apparatus of claim 14, wherein the at least one waveform includes three monotone waveforms, and the processor is further configured for each of the three monotone waveforms to:
- ramp an excitation amplitude to a desired amplitude;
- record the plurality of acceleration measurements and the plurality of force measurements for the period of time; and
- decrease the excitation amplitude until the force measurement is substantially zero.

* * * * *